US008574842B2

(12) United States Patent
Fan et al.

(10) Patent No.: US 8,574,842 B2
(45) Date of Patent: *Nov. 5, 2013

(54) DIRECT MOLECULAR DIAGNOSIS OF FETAL ANEUPLOIDY

(75) Inventors: Hei-Mun Christina Fan, Fremont, CA (US); Stephen R. Quake, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 445 days.

This patent is subject to a terminal disclaimer.

(21) Appl. No.: 12/644,388

(22) Filed: Dec. 22, 2009

(65) Prior Publication Data

US 2011/0151442 A1 Jun. 23, 2011

(51) Int. Cl.
*C12Q 1/68* (2006.01)
*C07H 21/02* (2006.01)
*C07H 21/04* (2006.01)

(52) U.S. Cl.
USPC ......... 435/6.11; 435/6.1; 435/6.12; 435/91.2; 536/24.31; 536/24.33

(58) Field of Classification Search
None
See application file for complete search history.

(56) References Cited

U.S. PATENT DOCUMENTS

| | | | |
|---|---|---|---|
| 5,888,740 | A | 3/1999 | Han |
| 6,159,685 | A | 12/2000 | Pinkel et al. |
| 6,180,349 | B1 | 1/2001 | Ginzinger et al. |
| 6,899,137 | B2 | 5/2005 | Unger et al. |
| 6,911,345 | B2 | 6/2005 | Quake et al. |
| 7,118,910 | B2 | 10/2006 | Unger et al. |
| 7,888,017 | B2 * | 2/2011 | Quake et al. ................. 435/6.12 |
| 2007/0077570 | A1 | 4/2007 | Lao et al. |
| 2007/0202525 | A1 | 8/2007 | Quake et al. |
| 2009/0053719 | A1 * | 2/2009 | Lo et al. ............................ 435/6 |

OTHER PUBLICATIONS

Fan et al. Am J Obstet Gynecol. 29th Annual Meeting of the Society for Maternal-Fetal Medicine. Available online Dec. 3, 2008. vol. 199, issue 8, Supplement A. p. S30, abstract #65.*
Lo et al. PNAS. 2007. 104:13116-13121 and supplemental content p. 1-18.*
Rahil et al. European J Human Genetics. 2002. 10: 462-466.*
Chunsun Zhang et al., "Miniaturized PCR chips for nucleic acid amplification and analysis: latest advances and future trends," Nucleic Acids Res. Jun. 18, 2007, vol. 35, No. 13, 4223-4237.
David L. Barker, et al., "Two Methods of Whole-Genome Amplification Enable Accurate Genotyping Across a 2320—SNP Linkage Panel," Genome Research 14:901-907 (2004).
A.R. Thornhill, et al., "ESHRE PGD Consortium 'Best practice guidelines for clinical preimplantation genetic diagnosis (PGD) and preimplantation genetic screening (PGS)'," Hum. Reprod. 2005 20(1):35-48.

Christopher M. Heaphy, et al., "Assessment of the Frequency of Allelic Imbalance in Human Tissue Using a Multiplex Polymerase Chain Reaction System," J. Mol. Diag., Apr. 2007, vol. 9, No. 2, 266-271.
Barbara Pertl, et al., 1999, "Rapid prenatal diagnosis of aneuploidy by quantitative fluorescent PCR on fetal samples from mothers at high risk for chromosome disorders", Mol. Hum. Reprod., 1999, vol. 5, No. 12, 1176-1179.
Esther H. Lips, et al., "Reliable High-Throughput Genotyping and Loss-of-Heterozygosity Detection in Formalin-Fixed, Paraffin-Embedded Tumors Using Single Nucleotide Polymorphism Arrays," Cancer Research, Nov. 15, 2005, vol. 65, No. 22, 10188-10191.
Yuri A. Berlin, "DNA Splicing by Directed Ligation (SDL)", Current Issues Molec. Biol., 1999, vol. 1, No. 1, 21-30.
Allan Caine, et al, "Prenatal detection of Down's syndrome by rapid aneuploidy testing for chromosomes 13, 18 and 21 by FISH or PCR without a full karyotype: a cytogenetic risk assessment", Lancet, Jul. 9, 2005, vol. 366, 123-128.
Y.M. Dennis Lo, et al., "Digital PCR for the molecular detection of fetal chromosomal aneuploidy", Proc. Natl. Acad. Sci., Aug. 7, 2007, vol. 104, No. 32, 13116-13121.
H. Christina Fan, et al., "Microfluidic digital PCR enables rapid prenatal diagnosis of fetal aneuploidy", Am. J. Obstet. Gynecol., May 2009, 200: 543e1-543e7.
Gill Bejerano, et al., "Ultraconserved Elements in the Human Genome," Science, May 28, 2004, vol. 304, 1321-1325.
Fiona M.F. Lun, et al., "Microfluidics Digital PCR Reveals a Higher than Expected Fraction of Fetal DNA in Maternal Plasma", Clinical Chemistry, 2008, vol. 54, No. 10, 1664-1672.
Luigi Warren, et al, "Transcription factor profiling in individual hematopoietic progenitors by digital RT-PCR", Proc. Natl. Acad. Sci., Nov. 21, 2006, vol. 103, No. 47, 17807-17812.
Kathy Mann, et al., "Strategies for the rapid prenatal diagnosis of chromosome aneuploidy", Eur. J. Hum. Genet., 2004, vol. 12, 907-915.
P.A. Auroux, et al., "Miniaturised nucleic acid analysis", Lab Chip, 2004, 4: 534-546.
Charleston W.K. Chiang, et al., "Ultraconserved Elements: Analyses of Dosage Sensitivity, Motifs and Boundaries," Genetics, Dec. 2008, vol. 180, 2277-2293.
V. Chan, et al., "Prenatal diagnosis of common single gene disorders by DNA technology," Hong Kong Med. J., 1997, vol. 3, No. 2, 173-178.

(Continued)

*Primary Examiner* — Carla Myers
(74) *Attorney, Agent, or Firm* — Rothwell, Figg, Ernst & Manbeck, P.C.

(57) ABSTRACT

Methods and materials for detection of aneuploidy and other chromosomal abnormalities using fetal tissue are disclosed. Results can be obtained rapidly, without cell culture. The method uses digital PCR for amplification and detection of single target sequences, allowing an accurate count of a specific chromosome or chromosomal region. Specific polynucleic acid primers and probes are disclosed for chromosomes 1, 13, 18, 21, X and Y. These polynucleic acid sequences are chosen to be essentially invariant between individuals, so the test is not dependent on sequence differences between fetus and mother.

10 Claims, 7 Drawing Sheets

(56) References Cited

OTHER PUBLICATIONS

Dongzhi Li, "A Multiplex Quantitative Fluorescent PCR Test for Prenatal Diagnosis of Hb Barts Hydrops Fetalis," Clinical Chemistry, 2007, 53:991-992.

W.C. Leung, et al., "Rapid aneuploidy testing (knowing less) versus traditional karyotyping (knowing more) for advanced maternal age: what would be missed, who should decide?", Hong Kong Med. J., Feb. 2008, 14:6-13.

Stmbalsk Agnieszka, et al., "Prenatal diagnosis—principles of diagnostic procedures and genetic counseling", Folia Histochemica et Cytobiologica, 2007, vol. 45, 11-16.

H. Christina Fan, et al., "Detection of Aneuploidy with Digital Polymerase Chain Reaction", Anal. Chem., 2007, 79:7576-7579.

* cited by examiner

SEQUENCE LISTING

<160> NUMBER OF SEQ ID NOS: 21

<210> SEQ ID NO 1
<211> LENGTH: 19
<212> TYPE: DNA
<213> ORGANISM: artificial
<220> FEATURE:
<223> OTHER INFORMATION: synthetic DNA primer

<400> SEQUENCE: 1
gttcggcttt caccagtct                                                    19

<210> SEQ ID NO 2
<211> LENGTH: 20
<212> TYPE: DNA
<213> ORGANISM: Artificial Sequence
<220> FEATURE:
<223> OTHER INFORMATION: synthetic DNA primer

<400> SEQUENCE: 2
ctccatagct ctccccactc                                                   20

<210> SEQ ID NO 3
<211> LENGTH: 20
<212> TYPE: DNA
<213> ORGANISM: Artificial sequence
<220> FEATURE:
<223> OTHER INFORMATION: synthetic DNA primer

<400> SEQUENCE: 3
ctcacctatc cacaatgcaa                                                   20

<210> SEQ ID NO 4
<211> LENGTH: 20
<212> TYPE: DNA
<213> ORGANISM: Artificial sequence
<220> FEATURE:
<223> OTHER INFORMATION: synthetic DNA primer

<400> SEQUENCE: 4
gggattcaag cgaattaaca                                                   20

<210> SEQ ID NO 5
<211> LENGTH: 20
<212> TYPE: DNA
<213> ORGANISM: Artificial sequence
<220> FEATURE:
<223> OTHER INFORMATION: synthetic DNA primer

<400> SEQUENCE: 5
ccagctggta cttggaagag                                                   20

<210> SEQ ID NO 6
<211> LENGTH: 19
<212> TYPE: DNA
<213> ORGANISM: Artificial sequence
<220> FEATURE:
<223> OTHER INFORMATION: synthetic DNA primer

<400> SEQUENCE: 6
tgtcgtatgt ggagccaac                                                    19

<210> SEQ ID NO 7
<211> LENGTH: 20
<212> TYPE: DNA

```
<213> ORGANISM: Artificial sequence
<220> FEATURE:
<223> OTHER INFORMATION: synthetic DNA primer

<400> SEQUENCE: 7
atgtttcgcc aacttctgag                                               20

<210> SEQ ID NO 8
<211> LENGTH: 20
<212> TYPE: DNA
<213> ORGANISM: Artificial sequence
<220> FEATURE:
<223> OTHER INFORMATION: synthetic DNA primer

<400> SEQUENCE: 8
agagctatgg cacaaacctg                                               20

<210> SEQ ID NO 9
<211> LENGTH: 20
<212> TYPE: DNA
<213> ORGANISM: Artificial sequence
<220> FEATURE:
<223> OTHER INFORMATION: synthetic DNA primer

<400> SEQUENCE: 9
gatgaggaag gcaatgatcc                                               20

<210> SEQ ID NO 10
<211> LENGTH: 20
<212> TYPE: DNA
<213> ORGANISM: Artificial sequence
<220> FEATURE:
<223> OTHER INFORMATION: synthetic DNA primer

<400> SEQUENCE: 10
ttggctttta ccaaataggg                                               20

<210> SEQ ID NO 11
<211> LENGTH: 20
<212> TYPE: DNA
<213> ORGANISM: Artificial sequence
<220> FEATURE:
<223> OTHER INFORMATION: synthetic DNA primer

<400> SEQUENCE: 11
cgcttaacat agcagaagca                                               20

<210> SEQ ID NO 12
<211> LENGTH: 20
<212> TYPE: DNA
<213> ORGANISM: Artificial sequence
<220> FEATURE:
<223> OTHER INFORMATION: synthetic DNA primer

<400> SEQUENCE: 12
agtttcgaac tctggcacct                                               20

<210> SEQ ID NO 13
<211> LENGTH: 20
<212> TYPE: DNA
<213> ORGANISM: Artificial sequence
<220> FEATURE:
<223> OTHER INFORMATION: synthetic DNA primer

<400> SEQUENCE: 13
cgccctgcca tgtggaagat                                               20
```

```
<210> SEQ ID NO 14
<211> LENGTH: 20
<212> TYPE: DNA
<213> ORGANISM: Artificial sequence
<220> FEATURE:
<223> OTHER INFORMATION: synthetic DNA primer

<400> SEQUENCE: 14
aggtgcatca tgggaacggc                                               20

<210> SEQ ID NO 15
<211> LENGTH: 20
<212> TYPE: DNA
<213> ORGANISM: Artificial sequence
<220> FEATURE:
<223> OTHER INFORMATION: synthetic DNA primer

<400> SEQUENCE: 15
tcagtgcctg cctggttccc                                               20

<210> SEQ ID NO 16
<211> LENGTH: 21
<212> TYPE: DNA
<213> ORGANISM: Artificial sequence
<220> FEATURE:
<223> OTHER INFORMATION: synthetic DNA primer

<400> SEQUENCE: 16
tcccaaactc tcctgccctg a                                             21

<210> SEQ ID NO 17
<211> LENGTH: 22
<212> TYPE: DNA
<213> ORGANISM: Artificial sequence
<220> FEATURE:
<223> OTHER INFORMATION: synthetic DNA primer

<400> SEQUENCE: 17
tgtttctctc tgcctgcact gg                                            22

<210> SEQ ID NO 18
<211> LENGTH: 25
<212> TYPE: DNA
<213> ORGANISM: Artificial sequence
<220> FEATURE:
<223> OTHER INFORMATION: synthetic DNA primer

<400> SEQUENCE: 18
tgtcgcactc tccttgtttt tgaca                                         25

<210> SEQ ID NO 19
<211> LENGTH: 20
<212> TYPE: DNA
<213> ORGANISM: Artificial sequence
<220> FEATURE:
<223> OTHER INFORMATION: synthetic DNA primer

<400> SEQUENCE: 19
aggcagctgt gtgaggtaac                                               20

<210> SEQ ID NO 20
<211> LENGTH: 20
<212> TYPE: DNA
<213> ORGANISM: Artificial sequence
<220> FEATURE:
<223> OTHER INFORMATION: synthetic DNA primer
```

```
<400> SEQUENCE: 20
aggcagctgt gtgaggtaac                                              20

<210> SEQ ID NO 21
<211> LENGTH: 20
<212> TYPE: DNA
<213> ORGANISM: Artificial sequence
<220> FEATURE:
<223> OTHER INFORMATION: synthetic DNA primer

<400> SEQUENCE: 21
aggcagctgt gtgaggtaac                                              20
```

DIRECT MOLECULAR DIAGNOSIS OF FETAL ANEUPLOIDY

FEDERALLY-SPONSORED RESEARCH OR DEVELOPMENT

This invention was made with Government support under contract HG002644 awarded by the National Institutes of Health. The Government has certain rights in this invention.

REFERENCE TO SEQUENCE LISTING, COMPUTER PROGRAM, OR COMPACT DISK

Applicants assert that the text copy of the Sequence Listing is identical to the Sequence Listing in computer readable form found on the accompanying computer file. Applicants incorporate the contents of the sequence listing by reference in its entirety.

BACKGROUND OF THE INVENTION

1. Field of the Invention

The present invention relates to the field of prenatal diagnosis of fetal aneuploidy.

In particular, the invention relates to a method for rapid prenatal diagnosis and detection of fetal aneuploidy by using a microfluidic digital PCR (polymerase chain reaction) that enables rapid, allele independent molecular detection of fetal chromosomal aneuploidy utilizing uncultured amniocytes and chorionic villus tissue.

2. Related Art

Presented below is background information on certain aspects of the present invention as they may relate to technical features referred to in the detailed description, but not necessarily described in detail. That is, individual compositions, components, or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

Fetal aneuploidy is a chromosomal abnormality that is a common cause of genetic disorder. It is represented by an abnormal number of chromosomes, such as an extra or missing chromosome. The incidence of fetal aneuploidy and other chromosome abnormalities is approximately 9 per 1000 live births [1] It is difficult to estimate their true incidence among all pregnancies due to the strong association with fetal miscarriage and stillbirth. The prevalence of chromosomal abnormalities clinically recognized early pregnancy loss is greater than 50%, and fetuses with aneuploidy account for 6-11% of all stillbirths and neonatal deaths [2]. Aneuploidy rates increase with advancing maternal age, yet despite advances in non-invasive prenatal screening, diagnosis of fetal chromosomal abnormalities is the most common indication for invasive prenatal testing [2].

Conventional cytogenetics is currently the gold standard for determining fetal karyotype and thereby detecting fetal aneuploidy. In this procedure, fetal cells obtained from amniotic fluid or chorionic villi are cultured and the karyotype is analyzed microscopically by observing condensed chromosomes during metaphase stage. While conventional cytogenetics can provide accurate information regarding chromosomal aberrations, it requires approximately 1-2 weeks for patients to obtain results. This time delay may result in both increased anxiety for expectant parents, and greater maternal morbidity should pregnancy termination be desired in the setting of abnormal results. Rapid and accurate molecular based detection of aneuploidy is thus highly desirable.

There have been several molecular diagnostic techniques developed for aneuploidy detection [3-5]. These techniques include Polymerase Chain Reaction (PCR), Fluorescence in Situ Hybridization (FISH), Quantitative Polymerase Chain reaction (PCR) or Short Tandem repeats, Quantitative Fluorescence PCR (QF-PCR), Quantitative real-time PCR (RT-PCR) dosage analysis, Quantitative Spectrometry of Single Nucleotide Polymorphism and Comparative genomic Hybridization (CGH). All these techniques provide tools for detection of aneuploidy, however some are invasive and most of them tend to be lengthy, labor intensive and some are allele-dependent, so that the results depend on the underlying genetics of the population.

In conventional RT-PCR, for example, one threshold cycle corresponds to a 2-fold change in copy number, making it exceedingly challenging to measure smaller changes [6], such as a 1.5-fold increase in number of a trisomic chromosome as compared to a normal disomic chromosome.

Thus it would be advantageous to have a more rapid and accurate method for detection of presence of abnormal chromosomes.

Currently, a number of rapid molecular diagnostic tests for fetal aneuploidy are available. The most widely validated ones are fluorescent in situ hybridization (FISH) [23-25], quantitative-fluorescent PCR (QF-PCR) [26-33], and multiplex ligation probe amplification (MLPA) [34-38].

In recent years, array comparative genomic hybridization (CGH) has also been introduced for the rapid prenatal diagnosis of aneuploidy and diseases associated with copy number variation [39-44]. While array CGH is able to provide genome-wide information on copy number variations at relatively high resolution, it requires several days for analysis and substantial amount of genetic materials [39, 44].

One of the methods that has been developed recently is a digital PCR. In digital PCR the amount of nucleic acids is quantified by counting amplification from single molecules [7, 8].

Digital PCR was first used on a multi-well plate format to detect mutations and allelic imbalances associated with cancer development [13-15], and this format has recently been applied to measure allelic imbalance in placental RNA with the goal of developing a noninvasive diagnostic for trisomy 21 [16]. A microemulsion platform was developed to increase the scale of the assay [17, 18], and it is now being used as a sample preparation technique for massively parallel sequencing [19]. However, all these previously described methods are cumbersome to implement, take a long time and require significant labor.

The emergence of microfluidics has led to the development of a commercially available microfluidic digital PCR platform that enables the simultaneous performance of approximately 9000 PCR reactions [20]. It has been used to study the gene expression of single progenitor cells [12], to relate gene function to identity in environmental microbes [21], and to measure trisomy in human cell lines [22].

It is therefore an object of this invention to provide a faster and more reliable method for detection of fetal aneuploidy, which can also be combined with other molecular tests. It is shown below that using a microfluidic digital PCR assay permits diagnosis of aneuploidy in amniotic fluid and chorionic villi within six hours.

SPECIFIC PATENTS AND PUBLICATIONS

Han U.S. Pat. No. 5,888,740 discloses a method for detection of fetal aneuploidy using synthetic internal controls that provide accuracy in determining chromosome copy number by strictly controlling the quantity of the internal control sequences and relative rates of polymerase chain reaction (PCR) for test versus control sequences.

Fan et al. US 2007/0202525 A1 published Aug. 30, 2007, discloses that digital PCR can be used to detect aneuploidy, such as the trisomy that causes Down Syndrome, in a mixture of fetal and maternal DNA.

Lo et al., "Digital PCR for the molecular detection of fetal chromosomal aneuploidy," *PNAS*, Aug. 7, 2007 vol. 104 no. 32 13116-13121 (Ref. [16]), discloses a digital PCR method which uses a real-time PCR assay. One method was termed "digital RCD," or digital relative chromosome dosage. A value was calculated by dividing the number of wells positive for the chromosome 21 locus by the total number of informative wells.

Fan and Quake, "Detection of aneuploidy with digital polymerase chain reaction," *Anal Chem.*, 2007 Oct. 1, 79(19): 7576-9, discloses that dPCR is generally applicable to any aneuploidy, does not depend on allelic distribution or gender, and is able to detect signals in mixtures of maternal and fetal DNA.

Mann et al., "Strategies for the rapid prenatal diagnosis of chromosome aneuploidy," *European Journal of Human Genetics*, (2004) 12, 907-915 discloses a one-tube QF-PCR test using the relative quantification of microsatellite alleles.

BRIEF SUMMARY OF THE INVENTION

The following brief summary is not intended to include all features and aspects of the present invention, nor does it imply that the invention must include all features and aspects discussed in this summary.

The present invention relates to the use of digital analysis to obtain numbers of different chromosomes in a sample comprising genomic DNA extracted from a fetal sample. By digital, it is meant that the results of a given reaction are binary, that is, there either is a target sequence present or there is not. A relatively large number of reactions are run, and the binary results are analyzed statistically to rule out random variation. Because the test is direct, that is, does not require cell culture or other lengthy sample preparation, it can be performed more rapidly than previous methods. This may be on the order of 6 hours, or 1-10 hrs depending on the protocol used. It is not necessary to culture the amniocytes or specifically prepare the sample beyond extracting the DNA. Because a binary result is obtained, it is only necessary to run sufficient cycles of amplification to produce a detectable result.

In certain aspects, the invention comprises a method for detecting a fetal chromosomal aneuploidy of a target chromosome, comprising the steps of: (a) obtaining a fetal sample, e.g., amniotic fluid or chorionic villi sample, containing genomic DNA (i.e., fetal DNA) including a target chromosome sequence and a reference chromosome sequence; (b) distributing said fetal sample into a plurality of reaction areas, e.g., wells or chambers, or spots. Each reaction area, as used in the present method, will contain on average not more than one target chromosome sequence and not more than one reference chromosome sequence; there will be a random fluctuation in numbers of sequences, and amounts of DNA per reaction area; (c) detecting whether said target chromosome sequence is present or absent in said plurality of reaction areas, said detecting comprising the step of detecting an invariant sequence, as defined herein, to produce a target count; (d) detecting presence and absence of said reference chromosome sequence in said plurality of reaction areas, said detecting comprising the step of detecting an invariant sequence, to produce a reference count; (e) obtaining sufficient numbers in said target count and said reference count to achieve statistical significance; and (f) comparing said target count to said reference count, whereby an abnormal difference between said target count and said reference count indicates fetal chromosomal aneuploidy in the target chromosome. If both the target chromosome and the reference chromosome are diploid, there will be essentially a zero difference between the two counts.

In certain aspects, the present invention comprises a method where the detecting step comprises amplification using a pair of primers and a detection probe for the target chromosome and another pair of primers and a detection probe for the reference chromosome. The amplification may take place in a digital per device and comprise the known steps of PCR, including denaturation, hybridization, and elongation.

In certain aspects, the present invention comprises a method where the PCR primers used hybridize to an ultraconserved sequence in the target chromosome and an ultraconserved sequence in the reference chromosome. "Ultraconserved sequences" are defined further below.

In certain aspects, the present invention comprises methods using one or more of the specific primers and probes described below. The target genes, if any, and chromosomes where the primers and probes hybridize are set forth in the table below.

In certain aspects, the present invention comprises a method where said detecting is of chromosome 13, 18, and 21, and said reference chromosome is chromosome 1.

In certain aspects, the present invention comprises a method where the step of comparing said target count to said reference count further includes the step of determining whether or not each total chromosome count is within a confidence interval of at least 99% in order to determine statistical significance of said abnormal difference. The exemplified method uses Poisson statistics for this purpose. For example, if a reference chromosome 1 should have a similar or identical count in euploidy, and a 50% higher count in trisomy, representing an abnormal difference.

In certain aspects, the present invention comprises a method for detecting a chromosomal aneuploidy of a target chromosome, comprising the steps of: (a) directly extracting genomic DNA from a sample, said DNA including at least one target chromosome sequence and at least one reference chromosome sequence; (b) distributing said fetal sample from step (a) concurrently into a plurality of reaction areas, each reaction area comprised in a microfluidic device and containing on average not more than one target chromosome sequence and not more than one reference chromosome sequence; (c) adding amplification primers and carrying out a plurality of amplification reactions concurrently in the plurality of reaction areas; (d) adding a label for detecting presence and absence of said target chromosome sequence in said plurality of reaction areas to produce a target count; (e) detecting presence and absence of said reference chromosome sequence in said plurality of reaction areas to produce a reference count; (f) obtaining sufficient numbers in said target count and said reference count to achieve statistical significance; and (g) comparing said target count to said reference count, whereby an abnormal difference between said target count and said reference count indicates fetal chromosomal aneuploidy in the target chromosome. Such a concurrent method is possible with devices which permit sample loading into a number of reaction panels having on the order of 700-800 chambers each. The number of reaction areas may generally be between 100 and 1000 in each panel; at least one panel is used for each chromosome.

In certain aspects, the present invention comprises a method in which the amplification reactions comprise heating and denaturing primers in the presence of a DNA polymerase, as in well-known PCR protocols. The sample (chromosomes), primers, probes, polymerase and reaction buffer including dNTPs are loaded into a device simultaneously.

In certain aspects, the present invention comprises a method where the amplification primers amplify regions of similar size in both the target chromosome sequence and reference chromosome sequence. This may be on the order of 50-120 bp; the primers and probes must be designed to work together and essentially simultaneously. The present method is preferably highly parallel, that is, all reactions are carried out in a single run.

In certain aspects, the present invention comprises a method wherein the detecting comprises contacting an amplified sequence with a fluorescent probe. In certain aspects of the invention, a fluorescent probe having one label is used for detecting amplified target sequence and a fluorescent probe having another label is used for detecting amplified reference sequence. In the exemplified method, red and green probes are used. Images of results from different probes can be combined to facilitate data interpretation, or the results can be computed numerically by imaging software.

DETAILED DESCRIPTION OF THE PREFERRED EMBODIMENTS

Definitions

Figure 1:
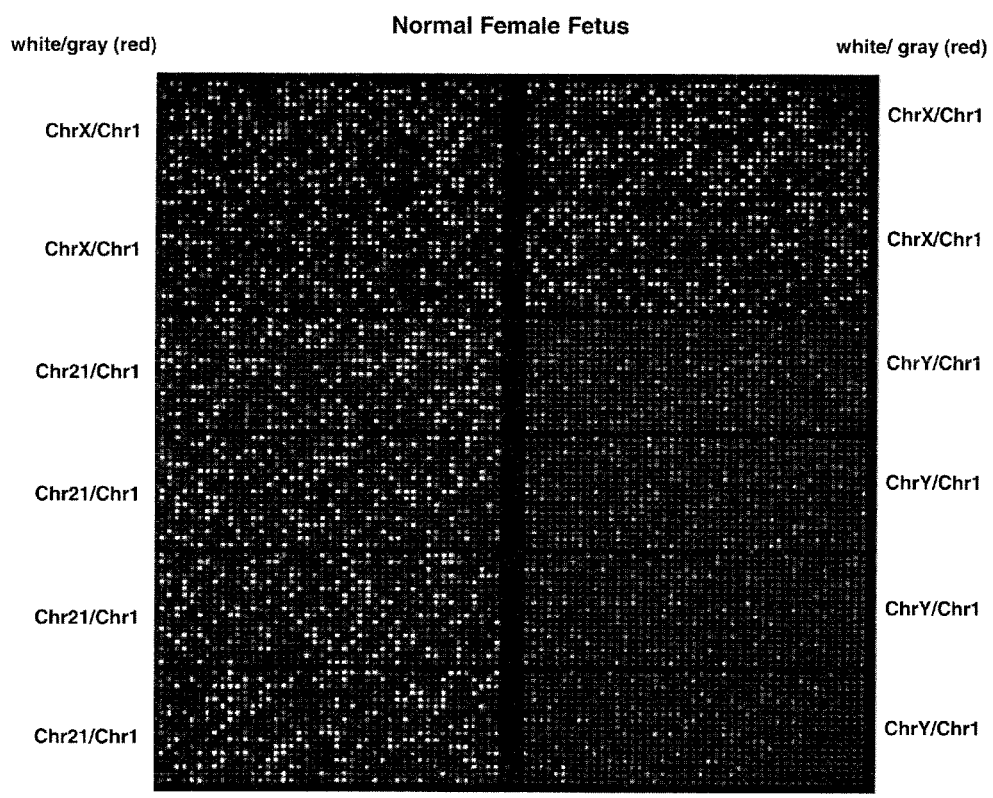
FIG. 1 is a sample false-color image of microfluidic digital PCR chip produced by overlaying the subtracted images in both fluorescent channels in normal female fetus (46 XX). The original photographs are in color and references to colors are to those in the original photographs, reproduced in *American Journal of Obstetrics and Gynecology*, 200(5) 543 e1-543 e7 (May 2009). FAM signal was shown in green (color as shown in in the above-referenced Journal), HEX signal was shown in red (color as shown in in the above-referenced Journal). A number of squares are illuminated, showing ratios of different chromosomes, i.e., chromosome X: Chromosome 1 (top 4 squares), 21 to 1 (bottom left four squares) and Y to 1 (bottom right four squares). A red square (color as shown in in the above-referenced Journal) represents a compartment containing amplification products giving out signal in the HEX channel (chromosome 1 locus). A green square in the above-referenced Journal represents a compartment containing amplification products giving out signal in the FAM channel (chromosome X, Y, or 21 loci, as labeled on the side of the image. A yellow square (color as shown in in the above-referenced Journal) is an overlap of a red and a green square (color as shown in in the above-referenced Journal). For the normal female fetus seen in FIG. 1, the number of green squares in the above-referenced Journal is comparable to that of red squares (color as shown in in the above-referenced Journal) in panels targeting chromosomes 21 and X. No green (color as shown in in the above-referenced Journal) are present in panels targeting chromosome Y (bottom right four squares).

Unless defined otherwise, all technical and scientific terms used herein have the same meaning as commonly understood by those of ordinary skill in the art to which this invention belongs. Although methods and materials similar or equivalent to those described herein can be used in the practice or testing of the present invention, the preferred methods and materials are described. Generally, nomenclatures utilized in connection with, and techniques of, cell and molecular biology, engineering and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The term "digital PCR" is used herein to refer to a method used to quantify the amount of specific nucleic acids in a sample by counting amplification from a number of single molecules. Digital PCR (polymerase chain reaction) is achieved by capturing or isolating each individual nucleic acid molecule present in a sample within many separate chambers, zones or regions that are able to localize and concentrate the amplification product to detectable levels. After PCR amplification, a count of chambers, zones or regions containing PCR end product is a direct measure of the absolute nucleic acids quantity. While the term refers to PCR, other types of amplification may be carried out in the individual chambers or regions, so long as the result is a detectible signal if a single molecule was initially present.

The term "microfluidic digital PCR" is used herein to refer to a method of digital PCR which uses a microfluidic system. As is known in the art, a microfluidic system comprises a number of fluidic elements, such as passages, chambers, conduit, valves, etc. configures to carry out or permit certain fluid handling and treatment operations, such as introduction of reagents, heating, cooling, etc. The system will generally have internal cross-sectional dimension, e.g., depth or width, of between about 10 nm and 500 µm. The present microfluidic digital PCR devices typically include a number of microscale channels, and preferably at least 50 and preferably on the order of hundreds of separate reaction chambers for individual PCR reactions to be carried out in parallel. The body structure of the microfluidic device may comprise a single component, or an aggregation of separate parts, e.g., capillaries, joints, chambers, layers, etc., which when appropriately mated or joined together, form the microfluidic device. Typically, the microfluidic devices described herein will comprise a top portion, a bottom portion, and an interior portion, wherein the interior portion substantially defines the channels and chambers of the device. In preferred aspects, the bottom portion will comprise a solid substrate that is substantially planar in structure, and which has at least one substantially flat upper surface, although one or more of these surfaces is generally provided with valve and other deformable structures. A variety of substrate materials may be employed. The substrate materials will generally be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and other reaction conditions needed for the amplification of a single nucleic acid. In some embodiments, the substrate material may include materials normally associated with the semiconductor industry in which such microfabrication techniques are regularly employed, including, e.g., silica based substrates such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material. Details on the construction of a suitable microfluidic device may be found for example in U.S. Pat. No. 6,899,137 to Unger, et al., issued May 31, 2005, entitled "Microfabricated elastomeric valve and pump systems;" U.S. Pat. No. 6,911,345 to Quake, et al., issued Jun. 28, 2005, entitled "Methods and apparatus for analyzing polynucleotide sequences;" U.S. Pat. No. 7,118,910 to Unger, et al., issued Oct. 10, 2006, entitled "Microfluidic device and methods of using same," etc.

The term "monosomy" is used herein to refer to lack of one chromosome of the normal complement. For example, monosomy of the sex chromosome (45,X) causes Turner syndrome. The designation 45, X means that there are 45 total chromosomes, with one X chromosome present.

The term "disomy" is used herein to refer to presence of two copies of a chromosome, which is a normal condition for human autosomes and for human females.

The term "trisomy" is used herein to refer to a presence of three copies, instead of the normal two; of a particular chromosome. Thus, for example, Down syndrome is characterized by the presence of three copies of chromosome 21 (Trisomy 21) and Kleinfelter's syndrome is characterized by the presence of the trisomy of the sex chromosome (Trisomy 47,XXX) for females or (Trisomy 47,XXY) for males. Other trisomies, namely Trisomy 13 and 18 are also found in live born humans. Trisomy 18, also called Edwards syndrome, is a chromosomal condition associated with severe intellectual disability and abnormalities in many parts of the body. Trisomy 13 syndrome, also known as Patau Syndrome, is a rare and the most severe of the possible autosomal trisomies with survival of not more than 3 days.

The term "fetal aneuploidy" is used herein to refer to an abnormal number of chromosomes observed in cells, which represents a type of chromosome abnormality, such as an extra or missing chromosome, that is a common cause of genetic disorder. The term includes monosomy, disomy and trisomy, except where such conditions are normal for a given chromosome. The term includes partial aneuploidy referring to a type of mosaicism in which some cells have a normal number of chromosomes and others an abnormal number. Also included, unless specified otherwise, is a type of partial aneuploidy where there is an unbalanced translocation, where a fragment of one chromosome is broken off and attached to another. For example, in some cases of Down's syndrome, there is a translocation of part of chromosome 21 onto chromosome 14. In a balanced translocation (found in the parent of an affected child) there is no additional genetic material, simply a smaller than normal chromosome 21 with a piece broken off, a normal second chromosome 21, a chromosome 14 with the broken piece of 21 attached, and a normal chromosome 14. This person appears entirely normal with no related health problems. However, if the normal 21 and the affected 14 (carrying material from the broken chromosome 21) are passed on from this person to an offspring, there is now extra genetic material from chromosome 21 (as the baby will have one normal 21 from each parent as well as the broken piece attached to 14). The translocation becomes 'unbalanced' and Down's syndrome results.

The present methods, applied to fetal aneuploidy, may also be applied to earlier stages of development, such as embryos, and may be used for pre-implantation genetic diagnosis (See, for details, Thornhill et al., "ESHRE PGD Consortium 'Best practice guidelines for clinical preimplantation genetic diagnosis (PGD) and preimplantation genetic screening (PGS)',"

*Hum. Reprod. Human Reproduction* 2005 20(1):35-48. Thus, references herein to "fetal DNA," "fetal samples," etc. are not limited to the strict definition of a fetus as an unborn vertebrate in later stages of development, but can, in certain embodiments, be applied to earlier or later subjects. If only a single genome is available, multiple primers for each chromosome will be employed, as described below.

The term "ploidy" is used herein to refer to a number of sets of chromosomes in the nucleus of a cell. In normal human body cells, chromosomes exist in pairs, a condition called diploidy.

The term "invariant sequence" is used herein to refer to a sequence that is conserved between individuals in sequence and copy number. It is of sufficient length to define primer and probe regions, i.e., primers of about 15-25 bp in length defining an amplicon about 50-100 bp in length, preferably about 70-90 bp in length, or about 500 bp in length, depending on the per system used. The sequence may tolerate point mutations and snps in the amplicon, but the primer and probe hybridization regions are not repeated or deleted, and are 90-100%, preferably 100%, identical between individuals, that is, without known human polymorphisms. An example of an invariant sequence is an ultraconserved element, as used in testing chromosomes 1, 13 and 18 in the present examples. The term "ultraconserved element" is used herein to refer to a segment of genomic DNA that is absolutely conserved in sequence (100% identity with no insertions or deletions) between individuals, although some copy number variation may exist, as reported in Chiang et al., "Ultraconserved Elements: Analyses of Dosage Sensitivity, Motifs and Boundaries," *Genetics*, Vol. 180, 2277-2293, December 2008. Such elements are also described in "Ultraconserved Elements in the Human Genome," by Bejerano G, et al. cited infra and in Reference 11. They also are conserved among orthologous regions of the human, rat, and mouse genomes. There are about 5500 sequences of over 100 bp identified in the article and the online supplement. Both the Watson strand and the Crick strand will, of course be conserved. Most ultraconserved elements are noncoding.

Other invariant sequences may be determined by reference to curated collections of DNA sequences, such as the Database of Genomic Variants (DGV; hyper text transfer protocol (http)(slash)(slash) projects.tcag.ca/variation.

The term "unique invariant sequence" refers to an invariant sequence that appears once in a genome, namely, once on a given chromosome. It may hybridize to primer that forms part of a primer pair whereby an invariant sequence is only amplified once per genome, i.e., will only produce one amplicon for one given chromosome. It may also be unique in that it is detected uniquely by a probe, even if amplification of different sequences occurs. While the use of primer pairs is contemplated, other methods of detection and/or amplification may not require primer pairs. It is preferred that the genome be human.

The term "statistical significance" refers to a result, namely a difference in numbers of positive results between a target and a reference that is not likely due to chance. The minimum chance level for statistical significance herein is 95% probability that the result is not due to chance, i.e., random variations in the data. A 95% confidence interval means that if the procedure for computing a 95% confidence interval is used over and over, 95% of the time the interval will contain the true parameter value (i.e., the true chromosome count). The preferred confidence level in the present method is 99% or 99.9%. Various methods, as is known, can be used to calculate statistical significance. The preferred and illustrated method here uses binomial probabilities and the Poisson distribution. A Poisson confidence interval can be calculated around a single number of observed events.

Overview

The present invention concerns prenatal diagnosis of fetal aneuploidy and a rapid method for detection thereof. The method utilizes microfluidic digital PCR that enables rapid, allele independent molecular detection of fetal chromosomal aneuploidy in uncultured amniotic fluid, amniocytes and chorionic villus tissue. The microfluidic digital PCR provides an assay for rapid detection of fetal aneuploidy from uncultured amniocytes and chorionic villi in 6 hours and the results of the assay are not allele-dependent, that is, they do not depend on any sequence difference between the fetus and a parent.

In the present method, a microfluidic device is used to deliver a PCR reaction mixture containing a sample of DNA templates obtained from the entire genomic content of a fetal cell. The DNA from the genome of a single cell would be considered one genome equivalent of DNA. Typically a number of genome equivalents are used in order to obtain a sufficient number of results for statistical significance to reside in different counts between a reference chromosome and a target chromosome suspected of being aneuploid. The reference chromosome is preferably chromosome 1 (or other chromosome necessary for development). If a small amount of sample DNA is available, multiple primers and probes to the same chromosome are used, and the mixture is multiplexed. That is, a single chromosome may be fragmented and distributed to a number of different reaction areas, and give a number of positive results corresponding to the ploidy of the chromosome in comparison to a reference chromosome similarly detected with multiple primer pairs and probes. The primers should be designed to individually hybridize to and only to selected target sequences, even when present in mixtures of dozens or hundreds of primers. Details on a highly multiplexed system capable of quantitating at least 300 different short target nucleic acids, wherein each short target nucleic acid is 18-30 nucleotides in length are found in Lao, et al. US 20070077570, published Apr. 5, 2007, entitled "Multiplexed Amplification of Short Nucleic Acids." Another multiplexed PCR protocol that may be used here is described in Harbecke et al., "A real-time PCR assay to identify and discriminate among wild-type and vaccine strains of varicella-zoster virus and herpes simplex virus in clinical specimens, and comparison with the clinical diagnoses," *J. Med. Virol.* 81(7): 1310-1322 (May 2009). In addition, whole genome amplification techniques may be used where very small samples are encountered, e.g., a single cell from a pre-implantation embryo. These are described in barker et al., "Two Methods of Whole-Genome Amplification Enable Accurate Genotyping Across a 2320-SNP Linkage Panel," *Genome Research* 14:901-907 (2004).

Multiplexing may also be used in connection with samples containing DNA from numerous cells. Multiplexing may use, for example, a number of primer/probe sets directed to invariant sequences on a target chromosome and a number of primer/probe sets directed to invariant sequences on one or more reference chromosomes.

The DNA sample is preferably derived directly from uncultured fetal cells, e.g., an amniotic fluid or chorionic villi sample. Extracted genomic DNA is quantitated and diluted. It is distributed into a large number of compartments such that on average there is less than one copy of template DNA sequence per compartment, i.e., less than 0.5 genome equivalents per compartment. The DNA in different compartments, or reaction areas, is treated so that a single molecule of a specific sequence can be detected. This is done using DNA amplification, preferably PCR. PCR is a well known procedure (See Zhang et al., "Miniaturized PCR chips for nucleic acid amplification and analysis: latest advances and future trends," Nucleic Acids Res. 2007; 35(13):4223-37 and Auroux, "Miniaturised nucleic acid analysis," *Lab Chip*, 2004, 4, 534-546, for detail on these procedures.

PCR products, which are only produced in compartments having a DNA template, are then fluorescently detected. By counting the number of compartments that display fluorescent signals at the end of the PCR reaction, the counts of the DNA template are obtained. Because digital PCR converts the exponential nature of PCR to linear signal, copy number changes smaller than 2-fold can be measured fast and with high precision. In addition, unlike conventional real-time PCR, quantification with microfluidical digital PCR is not affected by the efficiency of amplification. Microfluidical digital PCR used in the present examples utilized the 12.765 Digital Array microfluidic chip, commercially available from Fluidigm, South San Francisco, Calif. More information may be found on the device at world wide web (www) fluidigm-.com/pdf/fldm/FLDM_MRKT00066.pdf.

The present methods use PCR primers and fluorescent probes which bind specifically to the amplified PCR products. A variety of primers and probes may be used; as described below, the primers are designed to amplify sequences from a given chromosome, regardless of an individual's particular genotype. A variety of chromosome-specific amplification and/or detecting molecules can be envisioned given the present teachings. In a preferred embodiment, two different colors are used in the probes, one for a reference chromosome and one for a test chromosome, where aneuploidy is suspected. The two colors from the amplified sequences from the two different chromosomes can be counted and compared using automated imaging methods.

Compared to the previously known PCR methods, microfluidic digital PCR presents several advantages. The total time required for sample preparation and digital PCR analysis was approximately 6 hours (1 hour of manual sample preparation and 5 hours for instrument results). In terms of speed, this is comparable to FISH and QFPCR [3, 4], and better than MLPA, which requires overnight hybridization [34]. Unlike QF-PCR and MLPA, digital PCR is a single-step procedure and does not require post-PCR analysis with electrophoresis. Since PCR products are measured fluorescently and are never removed from the microfluidic device, there is no risk of product contamination between PCR reactions. Furthermore, digital PCR assays are universal and are not dependent on genetic polymorphisms; in contrast, the most common type of QF-PCR requires multiple polymorphic markers per chromosome to ensure informative results [3]. Digital PCR is also superior to FISH in that FISH is labor intensive and requires both trained personnel and intact cells for analysis [3, 4].

The results described below show that the present microfluidic digital PCR materials and methods result in the rapid diagnosis of the most common fetal aneuploidies in ongoing pregnancies, specifically Down syndrome (trisomy 21), Edwards syndrome (trisomy 18), and Patau syndrome (trisomy 13). The studies samples did not discover any cases of Turner syndrome (monosomy X), Klinefelter syndrome (XXY), and XYY syndrome, but based on obtained data, identification of these abnormalities with similar accuracy using microfluidic digital PCR is obtainable.

Figure 4:
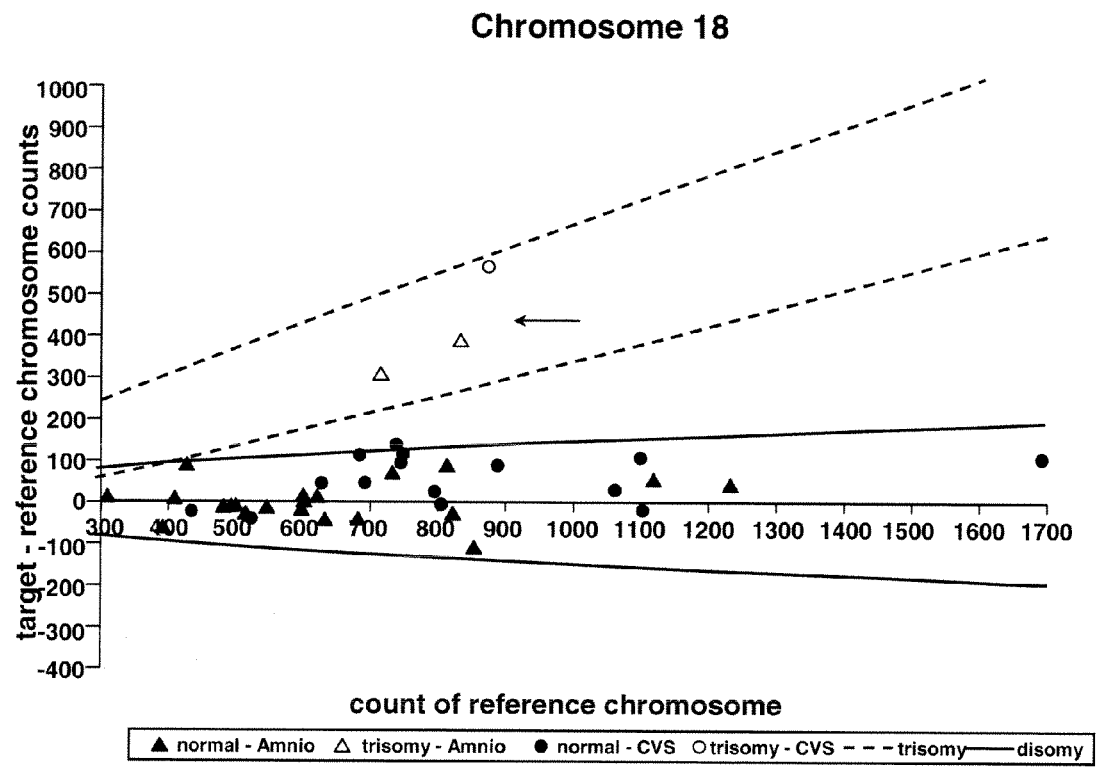
FIG. 4 is a graph that shows results of digital PCR for chromosome 18 as the target chromosome. Three cases of trisomy 18 were detected (see arrow). The rest were determined to be normal. For each sample, the difference between target chromosome counts is plotted against the reference chromosome count. The boundaries represent 99.9% confidence interval of each cases of ploidy.
Figure 5:
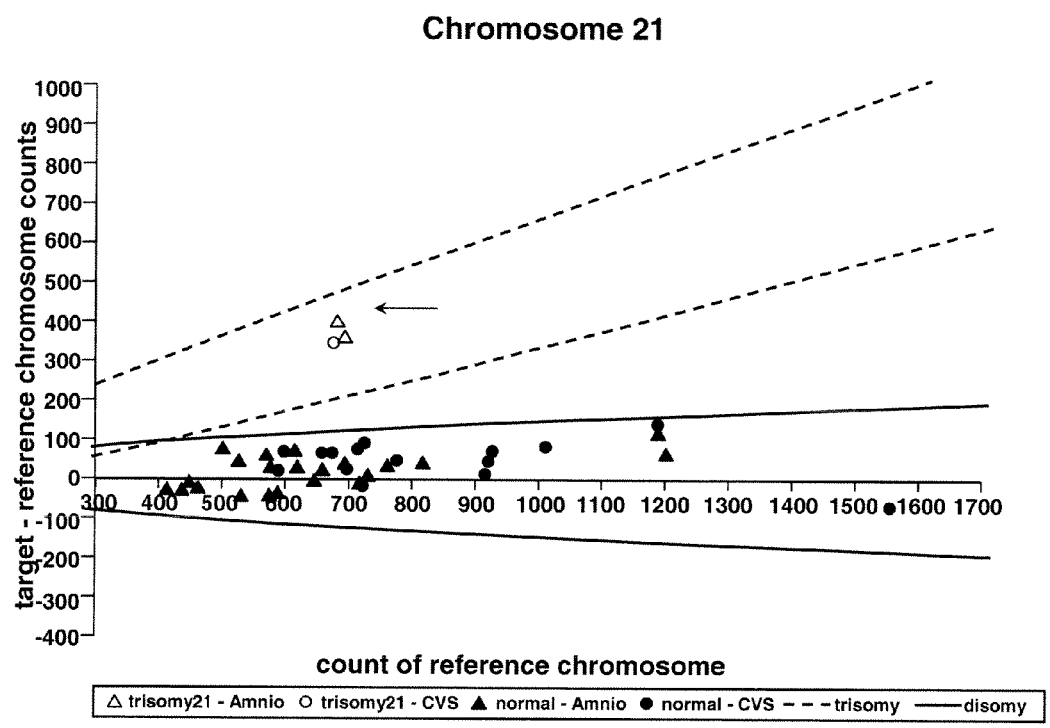
FIG. 5 is a graph that shows results of digital PCR for chromosome 21 as the target chromosome. Three cases of trisomy 21 were detected (see arrow). The rest were determined to be normal. For each sample, the difference between target chromosome counts is plotted against the reference chromosome count. The boundaries (dotted lines) represent 99.9% confidence interval of each cases of ploidy.

The ploidy of chromosome 18 for one of the samples was initially undetermined because it lay outside the threshold for normal ploidy (FIG. 4). Further testing with a separate chromosome 18 specific assay using primers to gene CNDP1 (carnosine dipeptidase 1 (metallopeptidase M20 family)) correctly determined the ploidy of the sample (data not shown; see SEQ ID NOs: 19-21). This result suggests that use of multiplexed primer sets and higher numbers of individual reaction areas are advantageous. More specifically, the initial testing of chromosome 18, described below, indicated a trisomy in certain samples, but the results were outside the statistical limits set. Repeating the test with a different primer/probe set resulted in data that confirmed the trisomies with statistical confidence. These data suggest that one may use a method here that involves multiple, different primer/probe sets for different chromosomes, and analyze the results either together, or separately.

The present digital PCR methods and array CGH (comparative genomic hybridization) can be used in a complementary fashion in order to provide rapid results on the most common genetic disorders via digital PCR, followed by more detailed but slower analysis with CGH. The present digital PCR methods can also be paired with other PCR based assays to provide equivalent diagnostic power to CGH. Details on carrying out CGH may be obtained from Pinkel et al., "Comparative Genomic Hybridization," U.S. Pat. No. 6,159,685, issued Dec. 12, 2000. Briefly, hybridization of the subject DNAs to reference chromosomes gives information on relative copy numbers of sequences. Some additional normalization is required to obtain absolute copy number information. One convenient method to do this is to hybridize a probe, for example a cosmid specific to some single locus in the normal haploid genome, to the interphase nuclei of the subject cell or cell population(s) (or those of an equivalent cell or representative cells therefrom, respectively). Counting the hybridization signals in a representative population of such nuclei gives the absolute sequence copy number at that location. Given that information at one locus, the intensity (ratio) information from the hybridization of the subject DNA(s) to the reference condensed chromosomes gives the absolute copy number over the rest of the genome.

Many amniotic fluid and CVS samples are contaminated with maternal DNA. While the incidence of fetal mosaicism is low (0.25% of amniocentesis specimens and 1% of chorionic villus specimens [2]), it has been shown that maternal cells are present in up to 20% of uncultured amniotic fluid samples [45]. The presence of contaminating euploid DNA in a sample from an aneuploid fetus would interfere with the accurate diagnosis of fetal aneuploidy. With contaminating euploid DNA, the ratio of counts of the abnormal chromosome to the reference chromosome would move to an intermediate value between 1.5 and 1.0, and the presence of trisomy DNA should be measurable by digital PCR by sampling a sufficient number of single DNA molecules. The present method may be run on different aliquots of a sample obtained from a single amniocentesis or CVS procedure, and can be used to distinguish maternal DNA contamination. It can also be combined with other DNA tests, such as a PCR test for Hb Barts Hydrops Fetalis (See, Li, "A Multiplex Quantitative Fluorescent PCR Test for Prenatal Diagnosis of Hb Barts Hydrops Fetalis," (*Clinical Chemistry*, 2007; 53:991-992), or alpha and beta thalassaemia, haemophilia A and B, Duchenne muscular dystrophy, Huntington's diseases, and spinal muscular atrophy (See Chan et al., "Prenatal diagnosis of common single gene disorders by DNA technology," *Hong Kong Med. J.*, 3(2):173-178 (1997).

Figure 6:
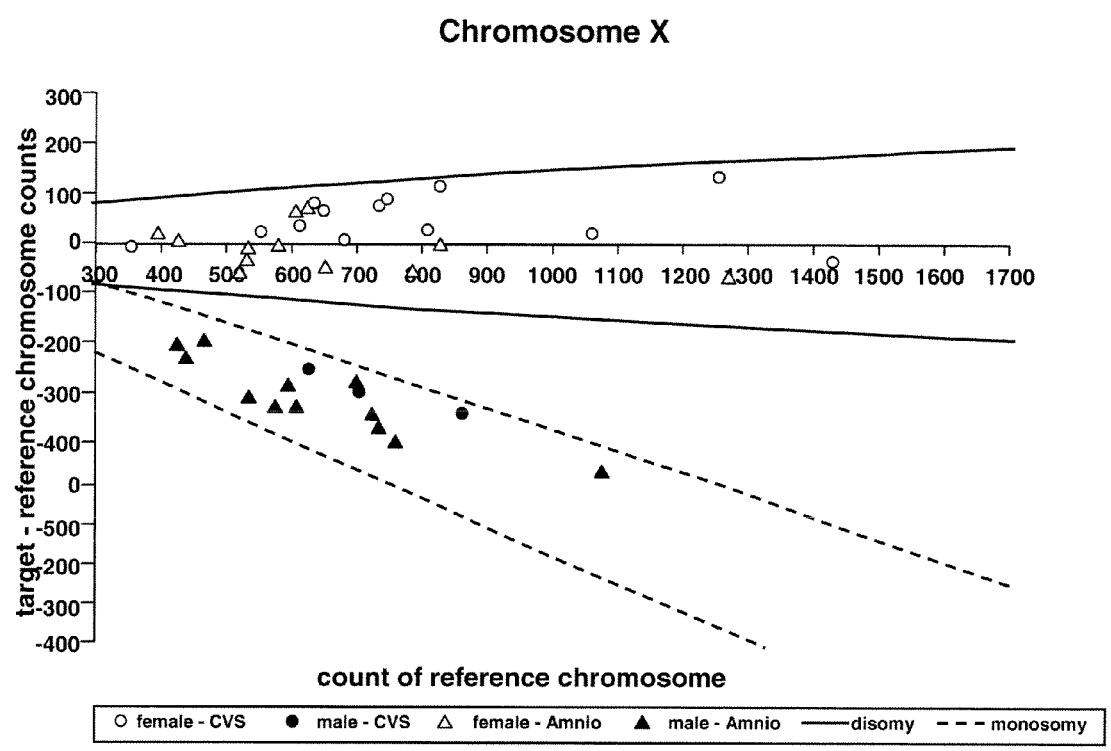
FIG. 6 is a graph that shows results of digital PCR for chromosome X as the target chromosome. All female samples fell within the region of disomy, while all male samples (shown between the dotted lines) lay within the region of monosomy. For each sample, the difference between target chromosome counts is plotted against the reference chromosome count. The boundaries (dotted lines for male and solid lines for female) represent 99.9% confidence interval of each cases of ploidy.

We have shown previously that digital PCR is capable of detecting trisomy in a background of contaminating euploid DNA [22]. In the present method, any significant maternal DNA contamination would be revealed by bias in the X chromosome signal from male samples; we did not observe any significant bias (FIG. 6). One of our amniotic fluid samples has a low level mosaicism (1 out of 15 cultured colonies was karyotyped as 45X while the remaining colonies were karyotyped as 46XX) and was interpreted as disomic for chromosome X by digital PCR. Such low-grade mosaicism would not be detectable with the current depth of sampling, but should be detectable by sampling a much larger number of single DNA molecules. Since the clinical and phenotypic ramifications of such mosaicisms, especially placental mosaicisms, are often difficult to predict, the present methods are considered most useful in cases where the fetus does not exhibit mosaicism, or an estimated 98.7% of all cases. Mosaicism may be confined to the placenta, and not present in fetal tissue. See *J Med Genet.* 1996 July; 33(7): 529-533. If mosaicism exists in the sample tested by the present methods, anomalous results for the affected chromosome will be obtained; that is, it will be present in some odd fractional proportion of the affected chromosome, which is neither diploid not fully aneuploid. Mosaicism can then be confirmed by further testing, using different numbers of starting fetal genetic material, and/or different sample sources, including fetal blood.

In practicing the present method one may use sufficient numbers of results to obtain a confidence interval of at least 99%, or higher, in order to determine statistical significance of an abnormal difference between a reference chromosome and the chromosome under test, e.g., the difference in counts between the reference chromosome and a test chromosome (e.g., 21, related to Down syndrome). In Example 5, z values derived from a normal curve of 3.29 were used for a 99.9% confidence interval. Other Z values, derived from the normal curve, may be used, for example 2.577 for a 99% confidence interval. The width of the 99.9% confidence interval was estimated for a disomy using $3.29 \times \sqrt{(N+N)}$, where N is the count of the reference chromosome, which is based on the total number of positive compartments from a given experiment, e.g., four of the panels shown in FIG. 1 from a device where each panel contains 765 compartments. The count of a target autosome (e.g., chromosome 21) should approximately equal the count of the reference chromosome. This can be seen in FIGS. 3-7. In the case of a trisomy, the width of the confidence interval is calculated using $\sqrt{(N+1.5N)}$, and in the case of a monosomy, $\sqrt{(N+0.5N)}$, where, again, N is the count of the reference chromosome.

Another limitation of digital PCR for rapid prenatal diagnosis is similar to those of FISH, QF-PCR, and MLPA in that it is not yet able to detect structural chromosomal abnormalities such as balanced translocations or inversions [4, 5]. We observed this effect in one of our CVS samples with a Robertsonian (13: 14) translocation. Similarly, improvements in the exemplified assay design are needed to detect 69, XXX triploidy, which is detectable by FISH and QF-PCR [46,47]. Although rare, these genetic defects may occur in approximately 1% of cases presenting for invasive diagnostic procedures [48, 49]. In 69, XXX, there is a complete haploid set of either maternal or paternal chromosomes. Further refinements of the primer and assay design will allow detection of these cases. One can include an assay for highly polymorphic markers that will give different results in different individuals. The haplotype of one or more maternal and paternal chromosomes can be distinguished. One may then detect an abnormal ratio of maternal and paternal alleles. Various methods are known for detecting allelic imbalance in cancer tissue, and these methods may be adopted here. See, Heaply et al., Assessment of the Frequency of Allelic Imbalance in Human Tissue Using a Multiplex Polymerase Chain Reaction System," *J. Mol. Diag.* 9(2) 266 (2007), describing the use of an Applied Biosystems AmpFISTR Identifiler multiplex polymerase chain reaction system to evaluate allelic imbalance at 16 unlinked, microsatellite loci located throughout the genome. In addition, single nucleotide polymorphism (SNP) arrays can be used for high-resolution genome-wide genotyping and loss of heterozygosity detection. See, Lips et al., "Reliable High-Throughput Genotyping and Loss-of-Heterozygosity Detection in Formalin-Fixed, Paraffin-Embedded Tumors Using Single Nucleotide Polymorphism Arrays," *Cancer Research* 65, 10188-10191, Nov. 15, 2005.

The current cost of aneuploidy detection with microfluidic digital PCR is approximately US $400, of which the majority is the cost of the microfluidic chips. However, the cost of digital PCR continues to decline over time as the technology of chip fabrication advances. In addition, the throughput and scale of microfluidic digital PCR should also improve considerably as better fabrication techniques allow more microfluidic compartments to be incorporated on a single chip. The robustness and simplicity of microfluidic digital PCR make it an attractive tool for rapid prenatal diagnostics and warrants further validation in larger clinical studies.

Alternative methods may be employed for obtaining counts representing a reference chromosome and a suspected aneuploid chromosome, given the present teachings, for determining the counts of fetal chromosomes and chromosome segments. For example, probes may be applied directly to the digitally diluted sample, as described in Castro et al., "Single-Molecule Detection of Specific Nucleic Acid Sequences in Unamplified Genomic DNA," Anal. Chem. 69(19):3915-3920 (1997). Also, rather than using the described invariant sequences, random short sequences (~20-30 bp) can be mapped to the chromosomes of interest and counted. By correcting for biases, such as those arising from sequencing methods, from chromosome size, from chromosome G/C content and the like, comparable counts can be obtained for a reference chromosome and a suspected aneuploid chromosome. Mapping to a reference human genome can be used to relate sequenced fragments to a specific chromosome. See Dappich et al, "Method For Identification Of Novel Physical Linkage Of Genomic Sequences," US 2009/0263798 A1 for a description of on method of mapping sequences to chromosomes and U.S. Pat. No. 6,975,943 entitled "Clone-array pooled shotgun strategy for nucleic acid sequencing," for a description of shotgun sequencing. Additional sequencing methodology is described in US 2009/0155781 A1 entitled "High throughput genome sequencing on DNA arrays." Since a reference human genome is available, sequencing may be directed only to specific areas of the genome, i.e., certain chromosomes, or the invariant sequences as described here.

EXAMPLES

Example 1

Microfluidic Digital PCR for Detection of Aneuploidy

This example demonstrates that digital polymerase chain reaction (PCR) enables rapid, allele independent molecular detection of fetal aneuploidy.

Twenty-four amniocentesis and 16 chorionic villus samples were used for microfluidic digital PCR analysis. Three thousand and sixty PCR reactions were performed for each of the target chromosomes (X, Y, 13, 18, and 21), and the number of single molecule amplifications was compared to a reference. The difference between target and reference chromosome counts was used to determine the ploidy of each of the target chromosomes.

FIG. 1 shows sample false-color images of microfluidic digital PCR chips. The chips were 12.765 Digital Array microfluidic chips obtained from Fluidigm, South San Francisco, Calif.). Each chip has 12 panels, which are compartmentalized into 765 nanoliter chambers by micro-mechanical valves. Based on the estimation of DNA concentration with quantitative real-time PCR, genomic DNA samples are diluted so that when loaded onto the microfluidic chip (Fluidigm), there is on average 1 template copy per every 3 (or more) chambers. PCR reaction mixture containing iQ Supermix obtained from BioRad, Hercules, Calif. or FastStart Universal Probe Master obtained from Roche, Indianapolis, Ind. together with primers and probes of chromosome 1 and 1 of the 5 target chromosomes is loaded onto each panel of the chip. Four panels are dedicated for each target chromosome. The reaction is performed on the BioMark System available from Fluidigm. Fluorescent images of the microfluidic chip are taken at the beginning and the end of the PCR. A computer program subtracts the initial image from the final image in each fluorescent channel and counts the number of positive compartments in each subtracted image.

Figure 2:
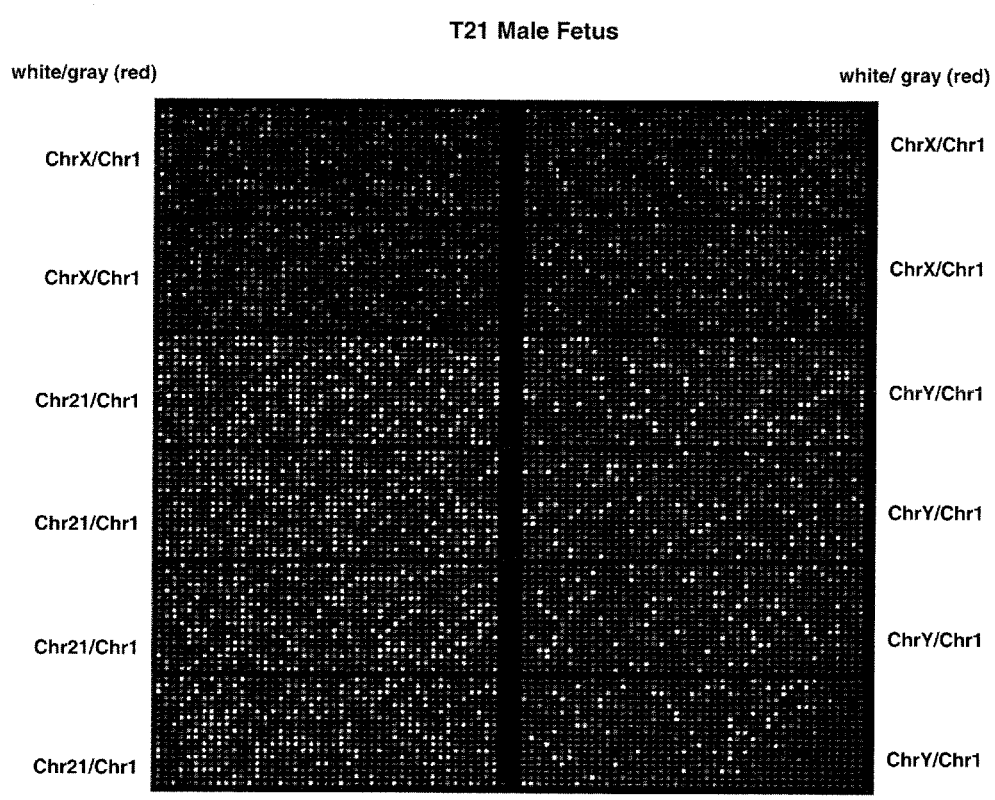
FIG. 2 is a sample false-color image of microfluidic digital PCR chip produced by overlaying the subtracted images in both fluorescent channels in male fetus with Trisomy 21 (47 XY+21). The original photographs are in color and references to colors are to those in the original photographs, reproduced in *American Journal of Obstetrics and Gynecology*, 200(5) 543 e1-543 e7 (May 2009). FAM signal is shown in green (color as shown in in the above-referenced Journal), HEX signal is shown in red (color as shown in the above-referenced Journal. A red square as shown in the above-referenced Journal represents a compartment containing amplification products giving out signal in the HEX channel (chromosome 1 locus). A green square (color as shown in in the above-referenced Journal) represents a compartment containing amplification products giving out signal in the FAM channel (chromosome X (top 2 rows, left and right sides), Y (right side, bottom panels), or 21 (left side, bottom four panels) loci, as labeled on the side of the image. A yellow square (color as shown in in the above-referenced Journal) is an overlap of a red and a green square (color as shown in in the above-referenced Journal). In the male fetus with T21 seen in FIG. 2, the number of green squares (color as shown in in the above-referenced Journal) is approximately half of that of red squares (color as shown in in the above-referenced Journal) in panels targeting chromosomes X and Y. More than expected number of green squares (color as shown in in the above-referenced Journal) is observed in panels targeting chromosome 21 (left side, bottom four panels). Comparison of green and red squares (color as shown in in the above-referenced Journal) counts reveals a ratio of approximately 3:2.
Figure 3:
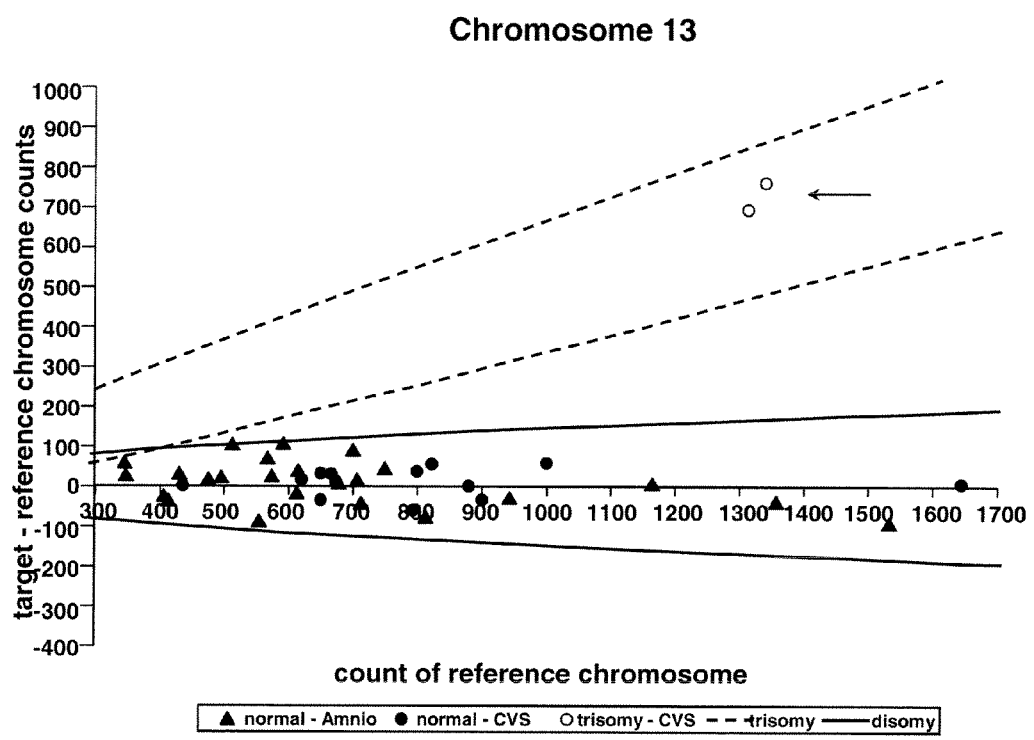
FIG. 3 is a graph that shows results of digital PCR for chromosome 13 as the target chromosome plotted as a line graph. All but two samples (shown by arrow) fell within the region of disomy. Two cases of trisomy 13 were detected. For each sample, the difference between target chromosome counts is plotted against the reference chromosome count. The boundaries represent 99.9% confidence interval of each cases of ploidy.

Images of the microfluidic digital PCR chips are shown in FIGS. 1 and 2. Signal from the FAM channel (target chromosomes) is shown in green (in original image) and that from the HEX channel (reference chromosome) is shown in red. FIG. 1 is from a sample identified as a female disomic for chromosome 21. The green counts from chromosome 21 and chromosome X are approximately equal to the red counts from chromosome 1. There is no signal from chromosome Y. FIG. 2 is from a sample identified as a male trisomic for chromosome 21. The green (original image) count from chromosome 21 is approximately 1.5 times greater than the red count from chromosome 1. The green counts from chromosome X and Y are approximately half of the red counts.

For each sample, the difference between target and reference chromosome counts was computed and plotted against the reference chromosome count, as shown in FIGS. 3-7. The 99.9% confidence interval for each cases of ploidy was constructed and used as a reference to classify the ploidy of each sample.

Figure 7:
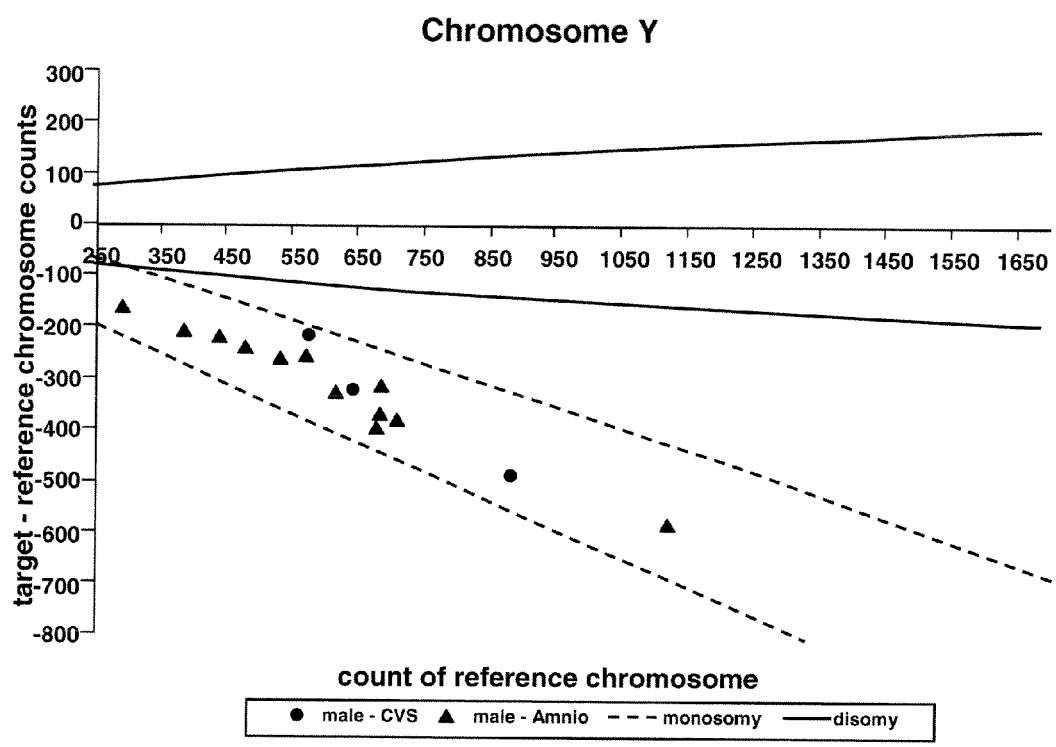
FIG. 7 is a graph that shows results of digital PCR for chromosome Y as the target chromosome. All male samples fell within the region of monosomy, indicated as in FIG. 6. None of the female samples showed amplification for chromosome Y assay. For each sample, the difference between target chromosome counts is plotted against the reference chromosome count. The boundaries represent 99.9% confidence interval of each cases of ploidy.

Digital PCR analysis accurately identified 2 cases of trisomy 13 (FIG. 3), 3 cases of trisomy 18 (FIG. 4), and 3 cases of trisomy 21 (FIG. 5) in the 40 samples analyzed. No cases of monosomy X, XXY, and XYY were observed. The rest of the samples were accurately identified as normal disomic for chromosome 13, 18, and 21, disomic and monosomic for chromosome X in the respective cases of female and male (FIG. 6), and monosomic for chromosome Y for the cases of male (FIG. 7).

Example 2

Sample Collection and Preparation

Samples for detection of aneuploidy were obtained from pregnant women having clinically indicated amniocentesis or chorionic villus sampling (CVS).

In cases of amniocentesis, 1-2 mL from the clinical sample was submitted separately for digital PCR analysis. A total of 40 samples, consisting of 24 amniotic fluid and 16 CVS samples, were processed. One twin pregnancy and 1 triplet pregnancy were enrolled.

Amniotic fluid was centrifuged at 14,000 rpm. Supernatant was removed and the cell pellet was resuspended in phosphate buffered saline (PBS). Chorionic villi were suspended in PBS. Next, genomic DNA was extracted from amniotic fluid and chorionic villi with QIAamp DNA Blood Mini Kit (Qiagen, Valencia, Calif.) according to the manufacturer's instructions. The QIAamp DNA Blood Mini Kit simplifies isolation of DNA from blood and related body fluids with fast spin-column or vacuum procedures (see flowchart "QIAamp Spin Column Procedure"). No phenol-chloroform extraction is required. DNA binds specifically to the QIAamp silica-gel membrane while contaminants pass through. PCR inhibitors such as divalent cations and proteins are completely removed in two efficient wash steps, leaving pure nucleic acid to be eluted in either water or a buffer provided with the kit. Optimized buffers lyse samples, stabilize nucleic acids, and enhance selective DNA adsorption to the QIAamp membrane. Alcohol is added and lysates loaded onto the QIAamp spin column. Wash buffers are used to remove impurities and pure, ready-to-use DNA is then eluted in water or low-salt buffer. The entire process requires only 20 minutes of handling time (lysis times differ according to the sample source). DNA was eluted into 100 μL and 200 μL of buffer for amniotic fluid and chorionic villi samples, respectively.

Example 3

Digital and Microfluidical Digital PCR

Digital and microfluidical PCR assays were performed as follows.

Taqman PCR assay was designed to amplify 1 region on each of the following chromosomes: 1, 13, 18, 21, X, Y. Chromosome 1 was chosen to be the reference chromosome since it is not associated with any aneuploidy observed in ongoing pregnancies [9]. The assay of chromosome 1 contained a probe labeled with a HEX fluorophore, while the assays for the target chromosomes (13, 18, 21, X, Y) each contained a probe labeled with a FAM fluorophore. The amplicon of each assay was chosen to lie outside of the regions with known copy number variation in healthy individuals [10]. In particular, the amplicons of chromosomes 1, 13, and 18 cover ultraconserved regions [11], which are rarely found to be associated with copy number variation in healthy individuals [10]. The amplicons were all 80-90 bp in length to reduce any amplification bias. The sequences of the primers and probes are listed in the Table, and were purchased from Integrated DNA Technology, Coralville, Iowa.

The concentration of extracted genomic DNA of each sample was estimated by quantitative real-time PCR with Taqman PCR assay designed for the locus on chromosome 1. A 5-point 10 fold dilution series of a commercially available genomic DNA sample, commercially available from Promega, Madison, Wis., was used to generate the standard curve for quantification.

The 12.765 Digital Array microfluidic chip, commercially available from Fluidigm, South San Francisco, Calif., was chosen as the digital PCR platform for this study. Each chip contains 12 panels, which are compartmentalized into 765 nanoliter chambers by micro-mechanical valves. Based on the estimation of DNA concentration with quantitative real-time PCR, genomic DNA samples were diluted such that when loaded onto the microfluidic chip (Fluidigm), there was on average 1 template copy per every 3 (or more) chambers. Nine microliters of PCR reaction mixture containing 1× iQ Supermix, commercially available from BioRad, Hercules, Calif., or 1× FastStart Universal Probe Master, commercially available from Roche, Indianapolis, Ind., 0.1% Tween-20, 300 nmol/L primers, and 150 nmol/L probes of chromosome 1 and 1 of the 5 target chromosomes was loaded onto each panel of the chip. Four panels were dedicated for each target chromosome. The reaction was performed on the BioMark System commercially available from Fluidigm, with the following thermal cycling protocol: 95° C. for 10 minutes, 40 cycles of 95° C. for 15 seconds, and 60° C. for 1 minute.

Fluorescent images of the microfluidic chip were taken at the beginning and the end of the PCR. A computer program, commercially available from Matlab; Mathworks, Natick, Mass., was written to subtract the initial image from the final image in each fluorescent channel and to count the number of positive compartments in each subtracted image.

Example 4

Primers and Probes

The sequences of the primers and probes used in the microfluidic PCR according to the invention are listed in Table 1. The primers and probes were purchased from Integrated DNA Technology, Coralville, Iowa.

TABLE 1

Sequences of primers and probes.

| Chr | Gene | Location | Forward Primer (5'-3') | Reverse Primer (5'-3') |
|---|---|---|---|---|
| 1 | EIF2C1 (u.c. 13)[a] | 1p34.3 | GTTCGGCTITCACCAGTCT (SEQ ID NO: 1) | CTCCATAGCTCTCCCCACTC (SEQ ID NO: 2) |
| 13 | MBNL2 (u.c. 356)[a] | 13q32.1 | CTCACCTATCCACAATGCAA (SEQ ID NO: 3) | GGGATTCAAGCGAATTAACA (SEQ ID NO: 4) |
| 18 | EHZF (u.c. 422)[a] | 18q11.2 | CCAGCTGGTACTTGGAAGAG (SEQ ID NO: 5) | TGTCGTATGTGGAGCCAAC (SEQ ID NO: 6) |
| 18 | CNDP1 | 18q22.3 | AGGCAGCTGTGTGAGGTAAC (SEQ ID NO: 19) | AGGCAGCTGTGTGAGGTAAC (SEQ ID NO: 20) |
| 21 | PRDM15 | 21q22.3 | ATGTTTCGCCAACTTCTGAG (SEQ ID NO: 7) | AGAGCTATGGCACAAACCTG (SEQ ID NO: 8) |
| X | non-coding | Xp22.3 | TCC GATGAGGAAGGCAATGA (SEQ ID NO: 9) | TTGGCTTTTACCAAATAGGG (SEQ ID NO: 10) |
| Y | SRY | Yp11.3 | CGCTTAACATAGCAGAAGCA (SEQ ID NO: 11) | AGTTTCGAACTCTGGCACCT (SEQ ID NO: 12) |

| Chr | Gene | Probe (5'-3') | 5' label | 3' label | Product Size (bp) |
|---|---|---|---|---|---|
| 1 | EIF2C1 (u.c. 13)[a] | CGCCCTGCCATGTGGAAGAT (SEQ ID NO: 13) | HEX | BHQ1 | 81 |
| 13 | MBNL2 (u.c. 356)[a] | AGGTGCATCATGGGAACGGC (SEQ ID NO: 14) | FAM | BHQ1 | 81 |
| 18 | EHZF (u.c. 422)[a] | TCAGTGCCTGCCTGGTTCCC (SEQ ID NO: 15) | FAM | BHQ1 | 87 |
| 18 | CNDP1 | AGGCAGCTGTGTGAGGTAAC (SEQ ID NO: 21) | FAM | BHQ1 | 90 |
| 21 | PRDM15 | TCCCAAACTCTCCTGCCCTGA (SEQ ID NO: 16) | FAM | BHQ1 | 89 |
| X | non-coding | TGTTTCTCTCTGCCTGCACTGG (SEQ ID NO: 17) | FAM | BHQ1 | 86 |
| Y | SRY | TGTCGCACTCTCCTTGTTTTGACA (SEQ ID NO: 18) | FAM | BHQ1 | 84 |

[a]Ultraconserved element: Annotation follows the online supplement to the paper Ultraconserved Elements in the Human Genome, Bejerano G, Pheasant M, Makunin I, Stephen S, Kent WJ, Mattick JS, Haussler D. Science, 304(5675), pp. 1321-1325 (2004), which is found at hyper text transfer protocol (http)(slash)(slash) users.soe.ucsc.edu/~jill/ultra.html. The primers used here as forward and reverse primers may be altered as known in the art. Since both strands on the chromosomal region are amplified, one may use primers according to the sequences given above which are the reverse complements of the above primers to achieve the same amplicons. In effect, the template strand is the complementary strand of that considered in the primer sequence given. One may use NCBI primer blast (hypertext transfer protocol :// world wide web ncbi.nlm.nih.gov/tools/primer-blast/) to design alternative primers.

Example 5

Statistical Analysis

Statistical analysis of the tested samples was performed as follows.

Counts of positive compartments were converted to counts of input template molecules based on the binomial approximation [12]. This correction arises from the fact that there will be compartments containing more than a single copy of template as the concentration of the template increases, and the count of positive compartments is an underestimate of the true count of input template molecules.

The difference between the target and reference chromosome corrected counts was computed. For the case of disomy, one would expect the difference to be approximately zero. For the case of trisomy, the difference would be positive and about half of the reference chromosome count, and in the case of monosomy the difference would be negative and about half of the reference chromosome count. We used Poisson statistics to construct confidence intervals for the count differences for every reference chromosome count and different cases of ploidy. The width of the 99.9% confidence interval of the count differences was estimated as $3.29*\sqrt{(N+N)}$ for disomy, $3.29*\sqrt{(N+1.5N)}$ for trisomy, and $3.29*\sqrt{(N+0.5N)}$ for monosomy, where N is the count of the reference chromosome. We then determined the ploidy of the target chromosome by looking at which region the data point was located. At the conclusion of the study period, the ploidy for each chromosome of each sample determined by digital PCR was compared to that of conventional karyotyping results to evaluate the diagnostic accuracy of digital PCR.

Example 6

Clinical Study for Detection of Aneuploidy

Pregnant women presenting for clinically indicated amniocentesis or chorionic villus sampling (CVS) at the Lucile Packard Perinatal Diagnostic Center of Stanford University were offered enrollment. Patients were recruited between January and June 2008, and informed consent was obtained prior to each procedure. In cases of amniocentesis, 1-2 mL from the clinical sample was submitted separately for digital PCR analysis. If maternal blood was visually apparent, the first 2 mL of amniotic fluid were discarded. In the absence of obvious contamination, the first 2 mL were often retained, which was the case for many of the samples. The exact proportion for these cases was not tracked. In cases of CVS, 1-2 mg was submitted separately for digital PCR analysis. Both transabdominal and transvaginal CVS approaches were employed, and the decision to perform one rather than the other was based on placental location and operator preference.

Study samples were labeled with specially assigned coded numbers and submitted for digital PCR analysis. The rest of each specimen was submitted to the Stanford cytogenetic laboratory for routine fetal karyotyping. Digital PCR analysis was performed with blinding to patients' personal information and without prior knowledge of the clinical karyotype results. Patients did not receive the digital PCR results but were notified of their cytogenetic karyotype results within 1 to 2 weeks as per Stanford University routine practice. The study was approved by the Stanford Institutional Review Board (IRB).

REFERENCES

1. Cunningham F, Hauth J, Leveno K, Gilstrap L, Bloom S, Wenstrom K. Williams obstetrics. New York: McGraw-Hill Professional; 2002: 942.
2. ACOG Practice Bulletin No. 88, December 2007. Invasive prenatal testing for aneuploidy. *Obstet Gynecol* 2007; 110: 1459-67.
3. Hulten M A, Dhanjal S, Pertl B. Rapid and simple prenatal diagnosis of common chromosome disorders: advantages and disadvantages of the molecular methods FISH and QFPCR. *Reproduction* 2003; 126:279-97.
4. Dudarewicz L, Holzgreve W, Jeziorowska A, Jakubowski L, Zimmermann B. Molecular methods for rapid detection of aneuploidy. *J Appl Genet* 2005; 46:207-15.
5. Shaffer L G, Bui T H. Molecular cytogenetic and rapid aneuploidy detection methods in prenatal diagnosis. *Am J Med Genet C Semin Med Genet* 2007; 145C:87-98.
6. Zimmermann B, Holzgreve W, Wenzel F, Hahn S. Novel real-time quantitative PCR test for trisomy 21. *Clin Chem* 2002; 48:362-3.
7. Kalinina O, Lebedeva I, Brown J, Silver J. Nanoliter scale PCR with TaqMan detection. *Nucleic Acids Res* 1997; 25:1999-2004.
8. Vogelstein B, Kinzler K W. Digital PCR. *Proc Natl Acad Sci USA* 1999; 96:9236-41.
9. Lathi R B, Westphal L M, Milki A A. Aneuploidy in the miscarriages of infertile women and the potential benefit of preimplantation genetic diagnosis. *Fertil Steril* 2008; 89:353-7.
10. Redon R, Ishikawa S, Fitch K R, et al. Global variation in copy number in the human genome. *Nature* 2006; 444:444-54.
11. Bejerano G, Pheasant M, Makunin I, et al. Ultraconserved elements in the human genome. *Science* 2004; 304:1321-5.
12. Warren L, Bryder D, Weissman I L, Quake S R. Transcription factor profiling in individual hematopoietic progenitors by digital RT-PCR. *Proc Natl Acad Sci USA* 2006; 103:17807-12.
13. Chang H W, Lee S M, Goodman S N, et al. Assessment of plasma DNA levels, allelic imbalance, and CA 125 as diagnostic tests for cancer. *J Natl Cancer Inst* 2002; 94:1697-703.
14. Zhou W, Galizia G, Lieto E, et al. Counting alleles reveals a connection between chromosome 18q loss and vascular invasion. *Nat Biotechnol* 2001; 19:78-81.
15. Zhou W, Goodman S N, Galizia G, et al. Counting alleles to predict recurrence of early-stage colorectal cancers. *Lancet* 2002; 359: 219-25.
16. Lo Y M, Lun F M, Chan K C, et al. Digital PCR for the molecular detection of fetal chromosomal aneuploidy. *Proc Natl Acad Sci USA* 2007; 104:13116-21.
17. Dressman D, Yan H, Traverso G, Kinzler K W, Vogelstein B. Transforming single DNA molecules into fluorescent magnetic particles for detection and enumeration of genetic variations. *Proc Natl Acad Sci USA* 2003; 100: 8817-22.
18. Diehl F, Li M, Dressman D, et al. Detection and quantification of mutations in the plasma of patients with colorectal tumors. *Proc Natl Acad Sci USA* 2005; 102:16368-73.
19. Margulies M, Egholm M, Altman W E, et al. Genome sequencing in microfabricated high-density picolitre reactors. *Nature* 2005; 437: 376-80.
20. Qin J, Jones R C, Ramakrishnan R. Studying copy number variations using a nanofluidic platform. *Nucleic Acids Res* 2008; 36:e116.

21. Ottesen E A, Hong J W, Quake S R, Leadbetter J R. Microfluidic digital PCR enables multi-gene analysis of individual environmental bacteria. *Science* 2006; 314:1464-7.
22. Fan H C, Quake S R. Detection of aneuploidy with digital polymerase chain reaction. *Anal Chem* 2007; 79:7576-9.
23. Kuo W L, Tenjin H, Segraves R, Pinkel D, Golbus M S, Gray J. Detection of aneuploidy involving chromosomes 13, 18, or 21, by fluorescence in situ hybridization (FISH) to interphase and metaphase amniocytes. *Am J Hum Genet* 1991; 49:112-9.
24. Klinger K, Landes G, Shook D, et al. Rapid detection of chromosome aneuploidies in uncultured amniocytes by using fluorescence in situ hybridization (FISH). *Am J Hum Genet* 1992; 51:55-65.
25. Ward B E, Gersen S L, Carelli M P, et al. Rapid prenatal diagnosis of chromosomal aneuploidies by fluorescence in situ hybridization: clinical experience with 4,500 specimens. *Am J Hum Genet* 1993; 52:854-65.
26. Mansfield E S. Diagnosis of Down syndrome and other aneuploidies using quantitative polymerase chain reaction and small tandem repeat polymorphisms. *Hum Mol Genet* 1993; 2: 43-50.
27. Pertl B, Yau S C, Sherlock J, Davies A F, Mathew C G, Adinolfi M. Rapid molecular method for prenatal detection of Down's syndrome. *Lancet* 1994; 343:1197-8.
28. Pertl B, Kopp S, Kroisel P M, et al. Quantitative fluorescence polymerase chain reaction for the rapid prenatal detection of common aneuploidies and fetal sex. *Am J Obstet Gynecol* 1997; 177:899-906.
29. Pertl B, Kopp S, Kroisel P M, Tului L, Brambati B, Adinolfi M. Rapid detection of chromosome aneuploidies by quantitative fluorescence PCR: first application on 247 chorionic villus samples. *J Med Genet* 1999; 36:300-3.
30. Pertl B, Pieber D, Lercher-Hartlieb A, et al. Rapid prenatal diagnosis of aneuploidy by 543.e6 American Journal of Obstetrics & Gynecology May 2009 quantitative fluorescent PCR on fetal samples from mothers at high risk for chromosome disorders. *Mol Hum Reprod* 1999; 5:1176-9.
31. Levett L J, Liddle S, Meredith R. A large-scale evaluation of amnio-PCR for the rapid prenatal diagnosis of fetal trisomy. *Ultrasound Obstet Gynecol* 2001; 17:115-8.
32. Mann K, Fox S P, Abbs S J, et al. Development and implementation of a new rapid aneuploidy diagnostic service within the UK National Health Service and implications for the future of prenatal diagnosis. *Lancet* 2001; 358:1057-61.
33. Mann K, Donaghue C, Fox S P, Docherty Z, Ogilvie C M. Strategies for the rapid prenatal diagnosis of chromosome aneuploidy. *Eur J Hum Genet* 2004; 12:907-15.
34. Schouten J P, McElgunn C J, Waaijer R, Zwijnenburg D, Diepvens F, Pals G. Relative quantification of 40 nucleic acid sequences by multiplex ligation-dependent probe amplification. *Nucleic Acids Res* 2002; 30:e57.
35. Slater H R, Bruno D L, Ren H, Pertile M, Schouten J P, Choo K H. Rapid, high throughput prenatal detection of aneuploidy using a novel quantitative method (MLPA). *J Med Genet* 2003; 40:907-12.
36. Gerdes T, Kirchhoff M, Lind A M, Larsen G V, Schwartz M, Lundsteen C. Computer-assisted prenatal aneuploidy screening for chromosome 13, 18, 21, X and Y based on multiplex ligation-dependent probe amplification (MLPA). *Eur J Hum Genet* 2005; 13:171-5.
37. Hochstenbach R, Meijer J, van de Brug J, et al. Rapid detection of chromosomal aneuploidies in uncultured amniocytes by multiplex ligation-dependent probe amplification (MLPA). *Prenat Diagn* 2005; 25:1032-9.
38. Boormans E M, Birnie E, Wildschut H I, et al. Multiplex ligation-dependent probe amplification versus karyotyping in prenatal diagnosis: the M.A.K.E. study. *BMC Pregnancy Childbirth* 2008; 8:18.
39. Sahoo T, Cheung S W, Ward P, et al. Prenatal diagnosis of chromosomal abnormalities using array-based comparative genomic hybridization. *Genet Med* 2006; 8:719-27.
40. Miura S, Miura K, Masuzaki H, et al. Microarray comparative genomic hybridization (CGH)-based prenatal diagnosis for chromosome abnormalities using cell-free fetal DNA in amniotic fluid. *J Hum Genet* 2006; 51:412-7.
41. Larrabee P B, Johnson K L, Pestova E, et al. Microarray analysis of cell-free fetal DNA in amniotic fluid: a prenatal molecular karyotype. *Am J Hum Genet* 2004; 75:485-91.
42. Rickman L, Fiegler H, Shaw-Smith C, et al. Prenatal detection of unbalanced chromosomal rearrangements by array CGH. *J Med Genet* 2006; 43:353-61.
43. Lapaire O, Lu X Y, Johnson K L, et al. Array-CGH analysis of cell-free fetal DNA in 10 mL of amniotic fluid supernatant. *Prenat Diagn* 2007; 27:616-21.
44. Bi W, Breman A M, Venable S F, et al. Rapid prenatal diagnosis using uncultured amniocytes and oligonucleotide array CGH. *Prenat Diagn* 2008; 28:943-9.
45. Winsor E J, Silver M P, Theve R, Wright M, Ward B E. Maternal cell contamination in uncultured amniotic fluid. *Prenat Diagn* 1996; 16:49-54.
46. Gersen S L, Carelli M P, Klinger K W, Ward B E. Rapid prenatal diagnosis of 14 cases of triploidy using fish with multiple probes. *Prenat Diagn* 1995; 15:1-5.
47. Schmidt W, Jenderny J, Hecher K, et al. Detection of aneuploidy in chromosomes X, Y, 13, 18 and 21 by QF-PCR in 662 selected pregnancies at risk. *Mol Hum Reprod* 2000; 6:855-60.
48. Peng H H, Chao A S, Wang T H, Chang Y L, Chang S D. Prenatally diagnosed balanced chromosome rearrangements: eight years' experience. *J Reprod Med* 2006; 51:699-703.
49. Cytogenetic analysis of chorionic villi for prenatal diagnosis: an ACC collaborative study of U.K. data. Association of Clinical Cytogeneticists Working Party on Chorionic Villi in Prenatal Diagnosis. *Prenat Diagn* 1994; 14:363-79. May 2009 American Journal of Obstetrics & Gynecology 543.e7

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein. Such reference is intended for the purpose of describing and enabling the method or material referred to.

What is claimed is:

1. A method for detecting a fetal chromosomal aneuploidy of a target chromosome, comprising the steps of:
   (a) obtaining a fetal sample containing genomic DNA including a target chromosome sequence and a reference chromosome sequence, said fetal sample being at least one of amniotic fluid, uncultured amniocytes and chorionic villus tissue;
   (b) distributing said fetal sample into a plurality of reaction areas, each reaction area containing on average not more than one target chromosome sequence and not more than one reference chromosome sequence;
   (c) detecting whether said target chromosome sequence is present in said plurality of reaction areas, said detecting comprising the step of detecting an invariant sequence using primers that hybridize to ultraconserved elements in genomic DNA, to produce a target count;
   (d) detecting whether said reference chromosome sequence is present in said plurality of reaction areas using primers comprising sequences according to SEQ ID NO: 1 and SEQ ID NO: 2 that hybridize to chromosome 1, said detecting comprising the step of detecting an invariant sequence, to produce a reference count;
   (e) obtaining sufficient numbers in said target count and said reference count to achieve statistical significance; and
   (f) comparing said target count to said reference count, whereby an abnormal difference between said target count and said reference count indicates fetal chromosomal aneuploidy in the target chromosome.

2. The method of claim 1 wherein said detecting step comprises amplification using one pair of primers and a detection probe for the target chromosome and another pair of primers and a detection probe for the reference chromosome.

3. The method of claim 1 wherein said target chromosome is one or more of chromosomes 13, 18, and 21, and said reference chromosome is chromosome 1.

4. The method of claim 1 wherein the step of comparing said target count to said reference count further includes the step of determining whether or not each count is within a confidence interval of at least 99% in order to determine statistical significance of said abnormal difference.

5. A method for detecting a chromosomal aneuploidy of a target chromosome, comprising the steps of:
   (a) directly extracting genomic DNA from a sample, said DNA including target chromosome sequence and reference chromosome sequence, said sample being a fetal sample of at least one of amniotic fluid, uncultured amniocytes and chorionic villus tissue;
   (b) distributing said fetal sample from step (a), concurrently into a plurality of reaction areas, each reaction area comprised in a microfluidic device and containing on average not more than one target chromosome sequence and not more than one reference chromosome sequence;
   (c) adding amplification primers, where one amplification primer set comprises sequences according to SEQ ID NO: 1 and SEQ ID NO: 2 that hybridize to reference chromosome 1 and one amplification primer set hybridizes to the target chromosome and where said amplification primers hybridize to ultraconserved elements in a genome and carrying out a plurality of amplification reactions concurrently in the plurality of reaction areas;
   (d) adding a label for detecting presence and absence of said target chromosome sequence and said reference chromosome sequence to produce a target count;
   (e) detecting presence and absence of said reference chromosome sequence in said plurality of reaction areas to produce a reference count;
   (f) obtaining sufficient numbers in said target count and said reference count to achieve a predetermined statistical significance in any difference between said target count and said reference count; and
   (g) comparing said target count to said reference count, whereby an abnormal difference between said target count and said reference count indicates fetal chromosomal aneuploidy in the target chromosome.

6. The method of claim 5 wherein said amplification reactions comprise heating and denaturing primers in the presence of a DNA polymerase.

7. The method of claim 5 wherein said amplification primers amplify regions of similar size in both the target chromosome sequence and reference chromosome sequence.

8. The method of claim 5 wherein the detecting comprises contacting an amplified sequence with a fluorescent probe.

9. The method of claim 8 wherein a fluorescent probe having one label is used for detecting amplified target sequence and a fluorescent probe having another label is used for detecting amplified reference sequence.

10. The method of claim 9 wherein said amplification primers comprise multiple primers directed to a single chromosome.

* * * * *